US009501317B2

(12) United States Patent
Kuruppu et al.

(10) Patent No.: US 9,501,317 B2
(45) Date of Patent: Nov. 22, 2016

(54) SYSTEM FOR FORMULATING TEMPORAL BASES FOR PROCESS COORDINATION IN A GENETICS RELATED PROCESS ENVIRONMENT

(71) Applicants: Indrajith Kuruppu, Wrestedt (DE); Don Damith Nadishan Colambathanthrige, Homagama (LK)

(72) Inventors: Indrajith Kuruppu, Wrestedt (DE); Don Damith Nadishan Colambathanthrige, Homagama (LK)

(*) Notice: Subject to any disclaimer, the term of this patent is extended or adjusted under 35 U.S.C. 154(b) by 0 days.

(21) Appl. No.: 14/433,509

(22) PCT Filed: May 9, 2014

(86) PCT No.: PCT/IB2014/061332
§ 371 (c)(1),
(2) Date: May 19, 2015

(87) PCT Pub. No.: WO2014/184720
PCT Pub. Date: Nov. 20, 2014

(65) Prior Publication Data
US 2015/0254101 A1    Sep. 10, 2015

(30) Foreign Application Priority Data

May 11, 2013   (WO) .................. PCT/IB2013/053825

(51) Int. Cl.
*G06F 9/46* (2006.01)
*G06F 9/48* (2006.01)
*G06F 19/10* (2011.01)

(52) U.S. Cl.
CPC ............. *G06F 9/4843* (2013.01); *G06F 19/10* (2013.01)

(58) Field of Classification Search
CPC .............................. G06F 9/4843; G06F 19/10
See application file for complete search history.

(56) References Cited

U.S. PATENT DOCUMENTS

| 2005/0154938 | A1* | 7/2005 | McLamb | G06F 11/1438 714/17 |
| 2008/0271030 | A1 | 10/2008 | Herington | |
| 2011/0016058 | A1* | 1/2011 | Pinchuk | G06Q 10/067 705/348 |
| 2012/0265787 | A1* | 10/2012 | Hsu | G06F 17/3064 707/780 |

FOREIGN PATENT DOCUMENTS

WO   PCT/IB2013/053825   11/2013

* cited by examiner

*Primary Examiner* — Camquy Truong

(57) ABSTRACT

Analytical methods and devices for detection of molecular processes, especially in genetics related environments are faced with the challenge of having to operate with the lack of coherent temporal frameworks that incorporate microscopic to macroscopic scale operations. Drawbacks in overcoming these challenges have resulted in substantial underutilization of resources and below optimum outcome as well. The present innovation as its technical solution to the problem outlined above discloses a computing based generic approach that facilitates incorporating operation of such processes as quantifiable entities in terms of a common temporal scale, thus establishing a coherent framework for coordinating operation of different processes that have varied temporal scales, namely, those occurring in temporal extents shorter as well as longer than its variable operational step enabling its adoption in a wide range of practical applications bringing multiple advantages.

13 Claims, 3 Drawing Sheets

SYSTEM FOR FORMULATING TEMPORAL BASES FOR PROCESS COORDINATION IN A GENETICS RELATED PROCESS ENVIRONMENT

FIELD OF INVENTION

The present invention relates to process coordinating systems, and more particularly, to establishing the respective temporal states in processes, including in facets of electromagnetism and action potential, corresponding with their respective resource utilisations and outcome in order to facilitate formulating a coherent basis for process management in genetics related contexts.

BACKGROUND

Analytical methods and devices for detection of molecular processes, especially in genetics related environments are faced with the challenge of having to operate with the lack of coherent temporal frameworks that incorporate microscopic to macroscopic scale operations. The key technical problem addressed by the proposed innovation can be outlined in relation to abovementioned lack of coherent frameworks mainly due to the fact that widely adopted approaches in the field of process management so far do not provide sound bases for incorporation of operation of processes that occur in temporal extents shorter than the smallest time unit adopted in such approaches (e.g. the operational steps in computing based process management systems), for example, transmission of electrical neurotransmissions in neurons and formulation of a plurality of microscopic scale bonds in a chemical process as entities in terms of a common temporal scale together with their respective associated processes. Due to lack of such bases for incorporating operation of these processes in terms of a common temporal scale, differentiation of their respective temporal extents on a consistent and robust context specific manner has not been possible so far, resulting in remarkably sub optimum utilisation of resources and outcome as well.

The present innovation as its technical solution to the problem outlined above discloses a computing based generic approach that facilitates incorporating operation of such processes as quantifiable entities in terms of a common temporal scale, thus establishing a coherent framework for coordinating operation of different processes that have varied temporal scales, namely, those occurring in temporal extents shorter as well as longer than its variable operational step enabling its adoption in a wide range of practical applications bringing multiple advantages as further described in detailed description below.

DETAILED DESCRIPTION

Figure 1:
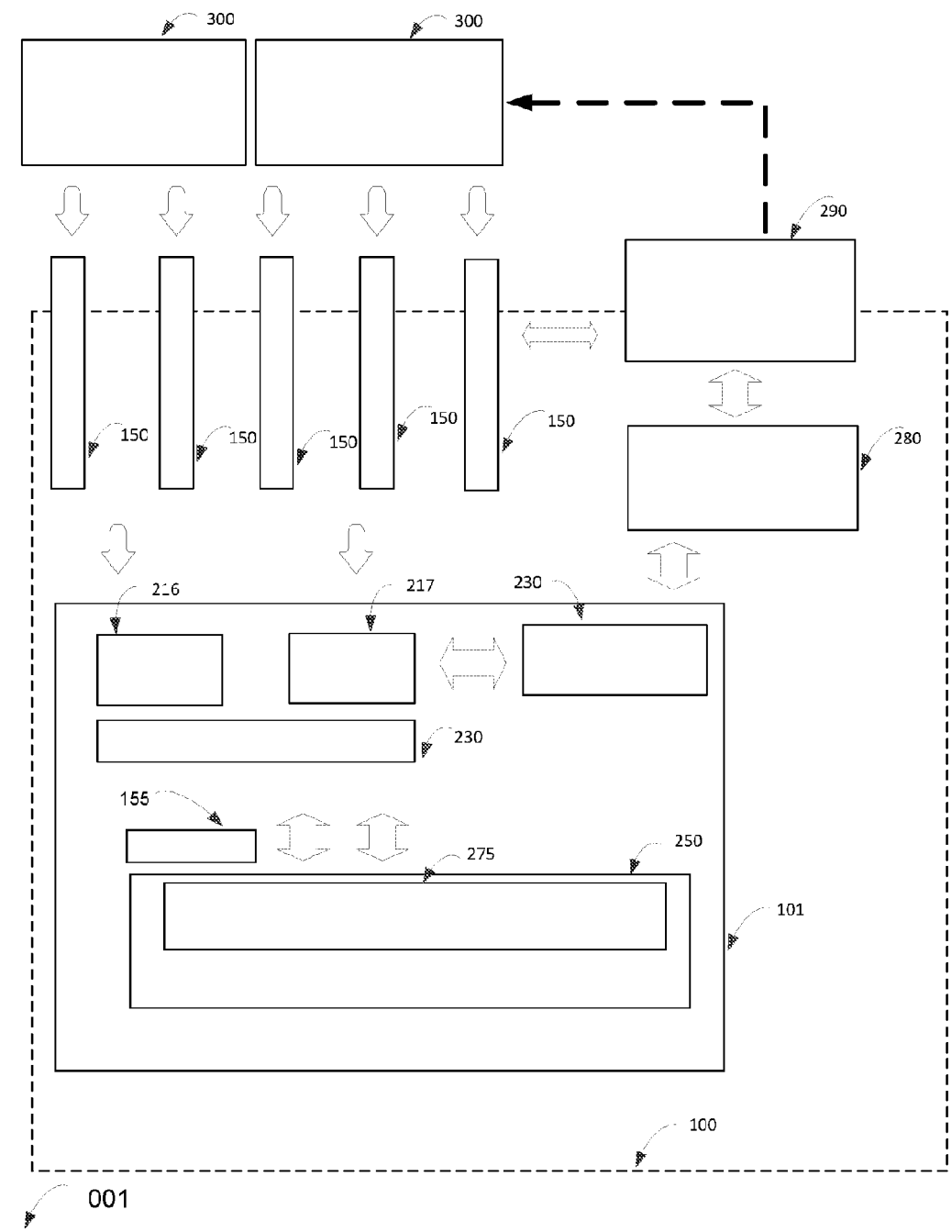
FIG. 1 illustrates a system that facilitates process coordination in accordance with an aspect of the innovation

The innovation is now described with reference to the drawings, wherein the reference numerals are used to refer to the same elements throughout. Specific details are set forth in order to provide a thorough understanding of the proposed innovation. Well known structures and devices are shown in block diagram form in order to facilitate describing the innovation.

The terms 'component', 'device', 'unit', 'engine' and 'system' in this application are intended to refer to a computing-related entity, either hardware, a combination of hardware and software, software or software in execution. For example, a system may be running on a processor or a controller, a processor, an object, an executable, a program, and/or a computing component. Both an application running on a server and the server can be a system. One or more systems can reside within a thread of execution, and a system can be localised on one location and/or, distributed between two or more locations. Each of the physical components in the system (100), unless otherwise mentioned, is accompanied by a variable clock apiece.

The term temporal state in the context of the present application refers to a derivation in the time dimension. A temporal state, while having a duration may also have a resource value. The term processes in the context of the proposed innovation refers to operations microscopic through macroscopic scales that are either physical in nature, for example, wave propagations and energy transfers, or involving chemical transformations, or both. A process may comprise one or more other processes. The term operation refers to occurring of a process, either individually or in conjunction with any of the other selected process, and in the context of the present innovation the terms operation of process and process derive similar meanings unless otherwise mentioned.

The terms process coordinating and process coordination refer to obtaining and analysing the information on operation of a plurality of processes, microscopic through macroscopic scales, and establishing said information in terms of a common temporal basis in order to facilitate conducting these processes with optimum performance in a resource saving manner. For the purpose of the present innovation, the term obtaining information on processes refers to receiving and transferring said information for analysis. In the context of the present innovation, the term process environment refers to a context wherein processes are associated with genetics based organisms i.e. plants, animals fungi, bacteria and archaea as well as viruses and the plurality of information on their operation disclose interrelations and the patterns of the interrelations that commensurate with one or more identifiable outcome. While the processes in a process environment may or may not be in the one and same physical context, the information of their operation as obtained by the novel instruments of the present innovation provides the rationale to be included, thus.

As set out for the purpose of outlining the present innovation, while the terms information and data derive similar meanings in the sense that both carry information, in the usage of the terms herein, however, information has been used to identify the contexts outside the system, i.e. before processing by the system, whereas the term data refers to contexts within the system, i.e. after processing. The term data handling refers to transferring, processing, storing and communicating as an output.

As used herein the terms to infer and inference refer generally to the process of reasoning about or inferring states of the process environment, and/or from a set of observations, as captured through events and/or information. Inference may be employed to identify a specific context or action, or, for example, can generate a probability distribution over states. The inference can be probabilistic, or the computation of a probability distribution over states, based on a consideration of information gathered. Inference may also refer to instruments employed for composing higher level action from a set of information. Such inference results in the construction of new actions from a set of observed and/or stored information, irrespective of whether they are correlated in close temporal proximity or not, and whether they originated from one or several sources.

In the context of the present innovation, the instruments that utilize such inferences based on analyses of observed and/or stored information as a basis for new actions, for example, in process coordinating in a process environment in a plant or a microbe colony, seek the formulation of these bases for action beyond the limitations in identifying the interrelations of the processes posed by predetermined formalisations. While recognizing that the formalisations related to temporal scales provide insights into the interrelations and their patterns, for example, behavioural patterns of different charged particles and/or wave propagation (e.g. in neurons and synapses in neurotransmission in an animal) commonly understood to be due to the different reference frames, deriving from theoretical framework provided by the theories on relativity, it must be mentioned that it has been a challenging task, so far, to utilize them to formulate such a wide range of interrelations and their patterns for action in order to optimize resource usage and outcome. This is evidenced through the rather limited usage of such formalisations (e.g. formalisations deriving from theoretical framework provided by the theories of relativity) in incorporating these interrelations into the present designs and operation of applications based on electromagnetism and action potential (e.g. linking action potential of a neuron with synaptic potential of another neuron), for instance.

Reference the drawings FIG. 1 illustrates a system (100) that coordinates a plurality of predetermined processes in a process environment (001). As revealed in FIG. 1, the system (100) includes a process coordinating component (101) that is connected with a plurality of process information devices (150) at the respective functional units (300) in the process environment (001) for obtaining information on a plurality of such processes in order to facilitate conducting process coordinating.

As the FIG. 1 illustrates the process coordinating component (101) further comprises a computing component (250) that employs a plurality of statistical and probabilistic analytical engines (SPAE) (275) for processing information obtained through the process information devices (150) in order to conduct process coordinating. The process coordinating component (101), as shown in FIG. 1, is further connected to a plurality of activating components (280) that transfer instructions formulated by the computing component (250) and the statistical and probabilistic engines (SPAE) (275) to a plurality of respective controlling components (290) that initiate and interrupt selected operations at the corresponding functional units (300).

One major overall goal of the present innovation is to enable the system (100) to establish a common temporal basis for operation of a plurality of selected processes in the process environment (001) including those occurring in durations lesser than the shortest variable of the variable operational step of said system (100) (e.g. electrical neurotransmission) in order for said system (100) for facilitating coordinating these processes effectively.

In accordance with the present innovation, as illustrated in FIG. 1, the novel techniques adopted therein facilitate obtaining information on a plurality of processes in the process environment (001) for conducting process coordinating. As further shown in FIG. 1, the information on processes obtained through process information devices (150) is received at a plurality of communicating components (216) each accompanied by a punctuation incorporating component (217) coupled to a buffering component (230) in the process coordinating component (101) which also comprises of a switching component (155) that initiates the computing component (250) at receiving a signal from signaling component (225) upon information on the predetermined processes reaching the process information devices (150).

Figure 2:
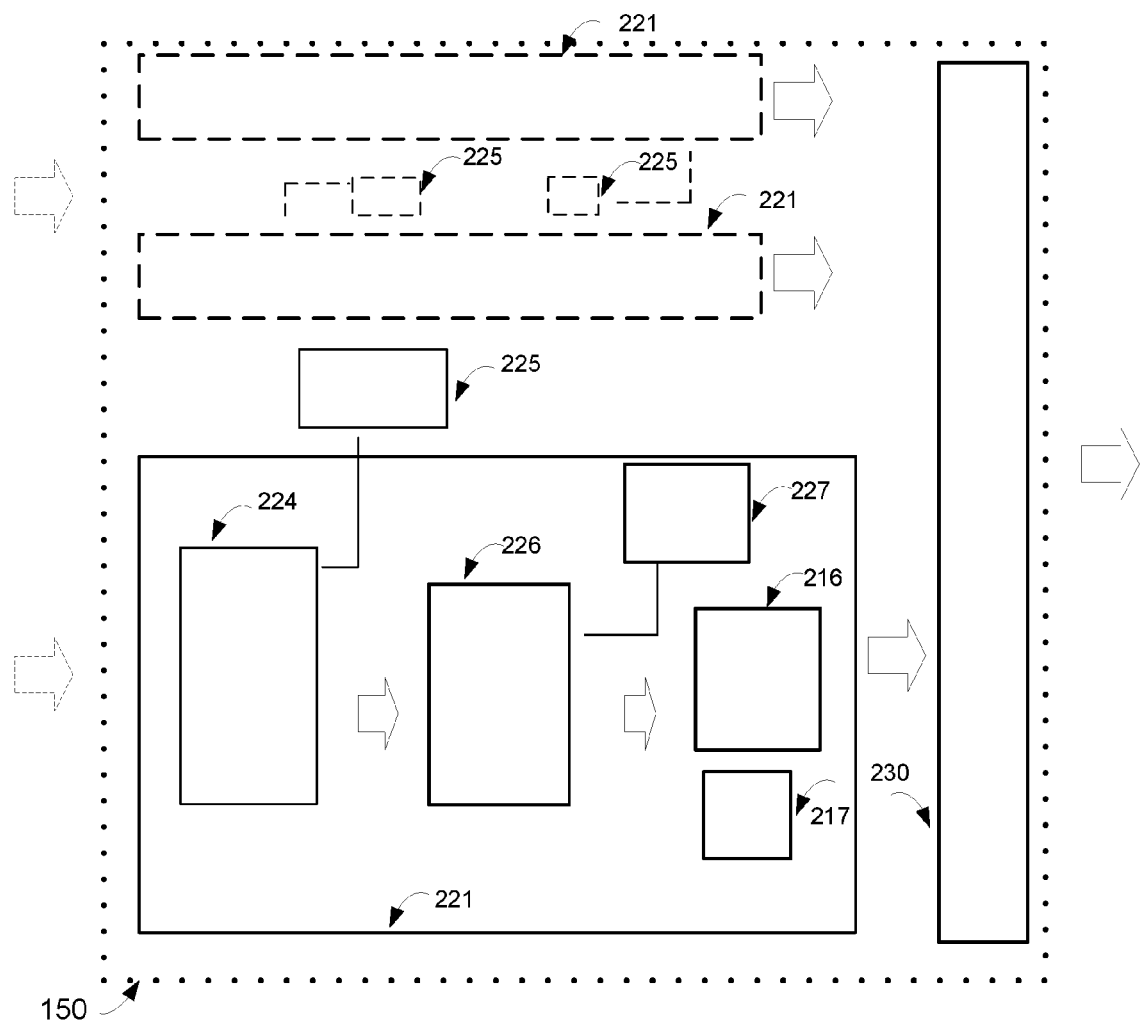
FIG. 2 illustrates a system that facilitates obtaining information on operation of processes from a plurality of information processing devices in accordance with an aspect of the innovation

In one key aspect of the present innovation, as FIG. 2 illustrates, each of the process information devices (150) includes a plurality of processing components (221) and a buffering component (230) for transferring information on these processes based on the instructions by the computing component (250) and the statistical and probabilistic engines (SPAE) (275). As FIG. 2 further illustrates, each of the processing components (221) comprises a plurality of reference characteristic identifying components (224), signaling components (225), reference characteristic receiving components (226), reference characteristic modificating components (227), communicating components (216) each accompanied by a punctuation incorporating component (217). In accordance with the present innovation, a signal transferred from a signaling component (225) upon commencing of information reaching the component (224) is received at the switching component (155), initiating the computing component (250) and the statistical and probabilistic engines (SPAE) (275) of the process coordinating component (101) to establish commands for activating information obtaining.

In one key aspect of the present innovation, the plurality of data selected processes are analysed in terms of the variable operational step of the computing component (250) and the statistical and probabilistic analytical engines (SPAE) (275). In conducting process coordination, in accordance with the present innovation in a process environment, for example, in a heart muscle tissue of a person, information on selected processes is obtained and analyses are made, including on transmitting of neurotransmission signal through neural cells that, in turn, initiates other related processes (e.g. neurotransmission through heart tissue cell membranes, endoplasmic reticulum releasing calcium ions to cytoplasm to initiate cell contraction, mitochondria providing energy for cardiac myocytes for contracting within the required rate) located at the respective functional units (300) (e.g. neurons that carry signals from brain to heart muscle tissue cells, heart muscle cells).

While activating obtaining information on selected processes the computing component (250) and the statistical and probabilistic analytical engine (SPAE) (275) analyse the selected pluralities of reference characteristics (e.g. amplitude and frequency of voltage pulses obtained as information on the process of varying concentration of ions in chemical neurotransmission at the heart muscle cells) of the respective information upon their receiving at the processing components (221) in order to establish the interrelations and the patterns of these interrelations of said characteristics of the information in terms of the variable operational step of said computing component (250). While the respective reference characteristics of the selected information are identified by the corresponding reference characteristic identifying components (224) and the respective characteristics are received by the relevant reference characteristic receiving components (226), in accordance with the present innovation, the computing component (250) based on the inferences by statistical and probabilistic analytical engines (275) initiates instructions for effecting a plurality of periodic interruptions with dynamically determined durations to each of said identifying by the respective characteristics by the components (224) and receiving by the corresponding characteristics by said components (226). In order to effect each of these interruptions, analyses of each of the identified characteristics by the respective components (224) and the transmissions of said characteristics between respective components (224) and the components (226) are conducted in terms of the variable operational step of the computing component (250).

In one key aspect of the present innovation, while each of the reference characteristics is identified by the relevant component (224) and received by the corresponding reference characteristic receiving component (226), the analyses are conducted based upon the inferences by statistical and probabilistic analytical engines (275) that establish the interrelations and the patterns of interrelations among similar analyses and their outcome, the computing component (250) instructs each of the reference characteristic modificating components (227) on the necessity and the extent to vary each of the corresponding references upon which the variable rate and the temporal extents of the analyzing of each of the reference characteristics is based, as well as each of the durations at which the respective interruptions to transferring each of said characteristics from each of the processing components (221) as data to the process coordinating component (101) to be effected.

Based on the inferences of statistical and probabilistic analytical engines (SPAE) that utilize the interrelations and patterns of interrelations of the above analyses and their outcome, the computing component provides instructions to the respective reference characteristic receiving component (226) to transfer a signal to the communicating component (216) and its accompanying variable clock to formulate the data corresponding to the characteristics received at the component (226) for transferring through the buffering component (230), to the process coordinating component (101). In formulating said data, in accordance with the present innovation, the computing component (250) and the statistical and probabilistic analytical engines (SPAE) (275) analyse the properties created upon receiving the information at the component (226) to be formulated as data, in order to establish the interrelations and the patterns of the interrelations of the respective characteristics in terms of their variable operational step for instructing the communicating component (216).

In accordance with the present innovation, these novel instruments utilising the novel features of obtaining information, mentioned supra, incorporate said transmission of different characteristics of information as processes in a specific process environment. Since a plurality of transmission of information (e.g. transmission of information on operation of electrical neurotransmission in a neural network) occur in temporal extents lesser than the shortest variable of operational steps of the computing component (250), in one key aspect of the present innovation, the novel instruments facilitate their incorporation as quantifiable entities in said process environments by effecting periodic interruptions to said obtaining information based upon the variable operational step of the computing component (250) and the statistical and probabilistic analytical engines (SPAE) (275) which, in turn, enables establishing robust bases for process coordinating across a wide range of different scales and applications.

Since each of the selected processes in a subject process environment (001) is closely associated with the corresponding information on its operation, as mentioned supra, in one key aspect of the present innovation, these novel instruments by formulating said transmission of information that occur in temporal extents lesser than the shortest variable of operational steps of the computing component (250) as measurable entities in terms of the common temporal basis that adopts the variable operational step of the computing component (250) and the statistical and probabilistic analytical engines (275) outline a framework for establishing said corresponding processes that take place in similar temporal extents that are lesser than said shortest variable of operational steps of the component (250) as quantifiable entities in terms of said common temporal basis as well.

In the fields related to process coordinating such as classical and quantum mechanics, it is among the well established principles to identify activities and processes in relation to time. In classical physics literature, while highlighting that it does not provide a 'fixed' backdrop, time is understood as a vital aspect in both non relativistic and relativistic situations. In the field of quantum mechanics, while making major advances in establishing formulations that broaden the understanding of the key properties, as well as the probabilities of the microscopic scale 'actors' and 'agents' assuming these properties, attributing for time has been part of well established principles among the different schools of thoughts associated with the discipline. It is evident, thus, that the temporal dimension has widely been considered a vital aspect in formulating bases in processes in microscopic through macroscopic scales.

In one key aspect of the present innovation, in order to facilitate establishing these processes on a common temporal basis, as mentioned supra, the variable operational step of the computing component (250) and the statistical and probabilistic analytical engines (SPAE) (275) is adopted for the analysis of information on said processes in the subject process environment (001). The novel instruments that conduct these analyses adopting the variable operational step of the computing component (250) and the statistical and probabilistic analytical engines (SPAE) (275), in accordance with the present innovation, formulate the interrelations and their patterns among said information on the respective processes based on said common temporal basis in order to derive the corresponding interrelations among the respective processes as well.

In situations where each of the reference characteristic identifying components (224) and each of the reference characteristic receiving components (226) in obtaining information on specific processes adopting the shortest variable of the operational step of the computing component (250) and the statistical and probabilistic analytical engines (275) the specific operations are complete (e.g. electrical neurotransmission among a group of neurons at electrical synapses) such processes are determined, for the purpose of the present innovation, to have occurred in temporal extents shorter than the shortest variable of said operational step of the component (250).

In order to utilise the interruptions to obtaining information for establishing said interrelations and their patterns the interrelations and their patterns among the plurality of information on the predetermined associations among the selected processes, in one key aspect of the present innovation, are established while each of the processes of which obtaining information is to be interrupted (e.g. electrical neurotransmission among a group of neurons) is in operation based upon the variable operational step of the computing component and the statistical and probabilistic analytical engines (SPAE). Similarly, a plurality of information on said associated processes is obtained and analyses are conducted, in accordance with the present innovation, during each of these periodic interruptions to each of the selected obtaining information of the selected processes that occur in temporal extents shorter than the shortest variable of the variable operational step of the computing component and the statistical and probabilistic analytical engines. In one key aspect of the present innovation, these novel instruments that conduct analysis of the plurality of information on selected processes utilise the interrelations and their patterns among information during these periodic interruptions to selected obtaining information as well as said close association between each of the plurality of processes and the corresponding information for formulating the interrelations and their patterns among the selected processes including those that occur in temporal extents lesser than the shortest variable of said operational step of the component (250) and their selected associating processes in a subject process environment.

As mentioned supra, these novel instruments effect interruptions to each of a plurality of obtaining information on selected processes in order to incorporate said processes into a common temporal basis, based upon the variable operational step of the computing component and the statistical and probabilistic analytical engines to facilitate coordinating processes. Based on the analyses of the interrelations and their respective patterns, in accordance with the present innovation, the novel mechanisms therein facilitate formulating interrelations of selected associating processes in relation to each of the temporal extents of such periodic interruptions to obtaining information on each of the selected processes that occur in durations lesser than said shortest variable of the operational steps, in terms of a common temporal basis that adopts the variable operational step of the computing component (250) and the statistical and probabilistic analytical engines (275).

In one key aspect of the present innovation, each temporal extent of the respective operations and the corresponding interruptions derived from the interrelations and their patterns among the selected associated processes (e.g. each temporal extent of electrical neurotransmission to selected cellular groups in the tissues of a heart muscle derived from the respective interrelations with the endoplasmic reticulum releasing calcium ions to cytoplasm, heart muscle contracting at the required rate) are established as collectives of the temporal states established in terms of the variable operational step of the computing component (250) and the statistical and probabilistic analytical engines (275).

These novel instruments adopted in the present innovation formulating the collectives of temporal states of the interruptions to each of these selected processes as derived through the interruptions to obtaining corresponding information based on the variable operational step of the computing component and the statistical and probabilistic analytical engines facilitate the incorporation of said processes into the process environment with quantifiable temporal extents of its own operation as well as quantifiable interrelations with selected associating processes in the specific process environment. As quantifiable entities incorporated in the subject process environment (100), the collectives of the respective temporal states of these operations (e.g. electrical neurotransmission to a group of cells in a heart muscle) disclose interlinks with the corresponding extents (e.g. values of electrical neurotransmission) of the associating processes (e.g. rate of release of calcium ions, rate of heart muscle contraction) in the context of the specific process environment, since, in accordance with the present innovation, the analyses and establishing interrelations are conducted upon a common basis, namely, the variable operating step of the computing component (250) and the statistical and probabilistic analytical engines (275).

In one key aspect of the present innovation, these novel instruments facilitate adopting the temporal extents of the interruptions to the selected processes, derived from interruptions to transfers of corresponding information, that occur in durations lesser than the smallest variable of the operational step of the computing component (250) (e.g. electrical and chemical neurotransmission) as a basis for quantifying of the processes identified as associating processes (e.g. release of calcium ions to cytoplasm, contraction of muscle tissue as associating processes) and their corresponding durations of operation in the context of the specific cellular process environment. In accordance with the present innovation, establishing temporal extents in selected operations in relation to these associated processes and their corresponding collectives of temporal states, formulated in terms of a common basis, namely, the variable operational step of the computing component (250) and the statistical and probabilistic analytical engines (275) facilitates incorporating and expressing them based upon a common temporal and resource framework.

In accordance with the present innovation, these novel instruments that formulate a wide range of processes in a cellular process environment based upon a common temporal and resource framework facilitate disclosing differentiations in temporal states and a selection of resource utilization and outcome in a robust manner across different energy forms, time scales and behavioural patterns of different 'actors and agents', microscopic through macroscopic scales. By establishing them based upon a common temporal and resource framework, the novel approaches adopted in the present innovation disclose, among other aspects, the differentiations in temporal states among selected processes during their operation.

By incorporating operation of microscopic through macro scale processes based on a common temporal and resource framework, in one key aspect of the present innovation, these novel instruments facilitate conducting process coordination at the respective functional units across different scales associated with the interrelations and their patterns of said processes in the subject process environment. In accordance with the present innovation, the novel instruments adopted therein while identifying these associations at the respective functional units of different scales facilitate approaching the smallest functional units in the respective process environments (e.g. an organelle in a cell in an animal organ, a DNA strand in a microbe) as independent and quantifiable operational entities in conducting process coordination.

These novel instruments, by approaching the smallest functional units as independent entities in relation to the specific context of the process environment and by adopting the temporal states derived from the variable operational step of the computing component and the statistical and probabilistic analytical engines, in one key aspect of the present innovation, expand the basis for process coordinating. By approaching these functional units as quantifiable entities and adopting the temporal states based upon the variable operational step of the computing component (250), these novel instruments adopted in the present innovation facilitate formulating the interrelations and their patterns of the selected processes in relation to each of these units (300) and their compositions in a scalable manner expanding the bases for process coordination. As these interrelations and their patterns are formulated in relation to different compositions (e.g. chemical and physical compositions) of the functional units in different scales, the novel instruments adopted in the present innovation enable establishing a basis for identifying each of said compositions that operates as required for different biological, botanical and genetic requirements in process environments wherein the processes such as, but not limited to different facets of electromagnetism, electrochemistry and action potential (e.g. different chemical, ion and particle compositions of sub cellular parts in animals and plants that transit from one predetermined chemical property level to another in different temporal extents upon the rate of change in pH level in their respective micro environment).

Figure 3A:
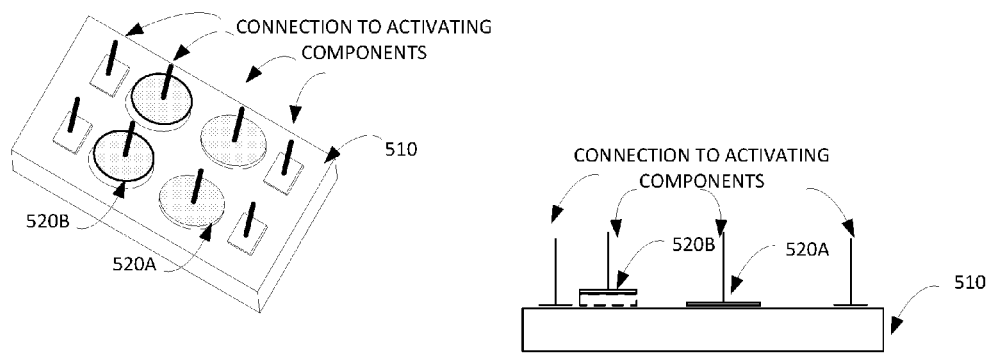
FIG. 3A illustrates a schematic representation of the smallest scale units, the elemental unit and the conductive unit and the insulated conductive unit that facilitate process coordination in accordance with an aspect of the innovation
Figure 3B:
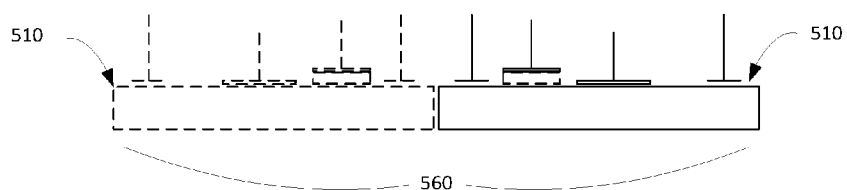
FIG. 3B illustrates a schematic representation of one of the smallest scale components, the elemental device that facilitates process coordination in accordance with an aspect of the innovation
Figure 3C:
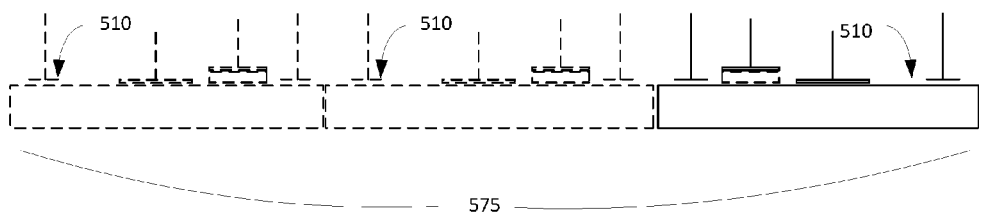
FIG. 3C illustrates a schematic representation of one of the smallest scale components, the elemental component, that facilitates process coordination in accordance with an aspect of the innovation

As obtaining information on the processes in a process environment is closely interlinked with other associated processes, including the respective constituent implements in the components and devices associated with said obtaining information establishing predetermined levels of electromagnetic properties (e.g. conductive and non-conductive properties) respectively for quantifiable temporal extents, and also with other selected processes (e.g. current gain-bandwidth corresponding to a fixed voltage and the respective charge carriers, for example, electrons receiving required energy quanta) in one key aspect of the present innovation, these novel instruments facilitate formulating interrelations and their patterns among these selected processes (e.g. establishing conductive and non-conductive properties in a semi conducting unit) at different scales. In one key aspect of the present innovation, the different scales at which these novel instruments coordinating the processes include the elemental units (510), the conductive units (520A), the insulated conductive units (520B), the elemental devices (560) and the elemental components (575) as illustrated in FIGS. 3A, 3B and 3C as well as their pluralities and combinations that form devices and components being utilized in different process environments, including, but not limited to switching and signal amplifying for facilitating formulation of these robust bases and expanding the scope of process coordination in cellular environments.

In accordance with the present innovation, the shortest variable of the operational steps of the computing component (250) and the statistical and probabilistic analytical engines (275) is lesser than the shortest temporal extent of transition from each of the dynamically determined levels of electromagnetic properties to any other dynamically determined level of such properties in each of these units (510, 520A and 520B) as instructed by the component (250) in the process environment.

In one key aspect of the present innovation, these novel instruments, upon supply of dynamically determined electrical energy inputs at each of these groupings of elemental units in the elemental devices and in the elemental components respectively enabling them attain the dynamically determined electromagnetic property levels, based on the comparisons with previous analyses of the respective properties, utilize these devices (560) and components (575) and their pluralities to transmit electromagnetic signals with dynamically determined characteristics for a wide range of applications.

Since the novel instruments adopted in the present innovation facilitate each of the groupings of elemental units assuming dynamically determined electrical functionalities (e.g. negative, positive, source) with dynamically determined levels of respective electromagnetic properties for variable temporal extents, the configurations of the elemental devices and the elemental components as well as their functions and capacities for transmitting electromagnetic signals can be optimized improving the utilization of resources and outcome as well. In optimizing the resources and outcome, in accordance with the present innovation, utilizing the activating components (280) the novel instruments adopted herein dynamically activate and deactivate the electrical interconnectivities of each of the elemental units associated with the respective dynamically formulated configurations of elemental devices and elemental components in order to maintain the optimum level of electromagnetic properties (e.g. just below threshold of conductivity, high conductivity) at each of said units, as determined by the computing component (250) based on the inferences of the statistical and probabilistic analytical engines (275).

The novel techniques adopted in the present innovation in dynamically configuring the elemental devices (560) and elemental components (575) facilitate their constituent groupings of elemental units (510) assume respective electromagnetic properties, including respective electrical functionalities upon supply of external electrical energy through combinations of respective pluralities of conductive units (520A) and insulated conductive units (520B). In configuring these elemental devices (560), elemental components (575) and their combinations, based upon the analyses, these novel instruments supply external electrical energy with the required combinations of electrical and temporal characteristics through the respective activating components (280) to each of the conductive units (520A) and the insulated conductive units (520B) in the dynamically formulated configurations, in order to establish respective electromagnetic property levels (e.g. just below threshold of conductivity) with dynamically determined properties for dynamically determined temporal extents. In one key aspect of the present innovation, as each of the conductive units (520A) and the insulated conductive units (520B) are connected to one or more elemental units (510) that are configured in their groupings with dynamically determined electrical functionalities for forming the elemental devices (560) and elemental components (575), the novel techniques adopted in the present innovation dynamically determine the specific numbers, compositions and temporal extents of said conductive units and insulated conductive units to be utilized, in order for establishing the dynamically determined levels of electrical properties that facilitate transmission of electromagnetic signals and the interruptions to such transmissions.

In one key aspect of the present innovation, in different operational contexts (e.g. information handling, energy management) deriving from the increased possibilities of combinations of supply of external electrical energy for dynamically determined temporal extents with variable electrical characteristics, these novel techniques formulate greater operational opportunities for each of the elemental units and their different formations that combine to formulate each of the electrical functionalities (e.g. source, negative, drain, positive, gate, base) assisted by the combinations of respective conductive units to assume a plurality of functions according to different requirements and applications, based on the instructions by the computing component and the statistical and probabilistic analytical engines. Based upon that, in accordance with the present innovation, each of the elemental devices, elemental components and their scalable combinations are able to assume multi functional roles as well, since the novel instruments therein utilize the varying temporal and other related characteristics in establishing the predetermined levels of respective electromagnetic properties in the constituent elemental units in pluralities of combinations, upon being supplied with electricity in a variety of combinations of electrical characteristics (e.g. voltage, current) for different temporal extents, thus enabling optimizing the types, numbers and permutations in corresponding temporal extents in the operation of respective components and their parts. Dynamically formulating each of the plurality of electromagnetic signals in relation to the specific applications, in one key aspect of the present innovation, in terms of the minimum required energy levels, with optimum time intervals between such signals facilitate creating these greater operational opportunities, as the novel instruments adopted in the present innovation formulate the configurations of these units and transmission of said signals maintaining the optimum electrical energy levels in such units (e.g. threshold conductivity level in elemental units, threshold electrical field emitting level in insulated conductive units) engaged in each of said signal transfers as well as those units not engaged in said transfers at the required levels for the required temporal extents, thus avoiding electrical energy leakages, that cause errors and energy losses at these smallest scales as well.

By facilitating employing a scalable unit of analysis for formulating interrelations and their patterns of the selected processes these novel instruments adopted in the present innovation enable establishing a basis for identifying the respective collectives of functional units of each type required for maintaining the predetermined functions in the subject process environment. By employing a scalable unit of analysis for process coordinating, these novel instruments adopted in the present innovation facilitate an entire range of novel operational features and outcome at microscopic scale of composing (e.g. formulating genetic compositions in smallest functional units - smallest segments of groups of cells in the phloem in a plant that dynamically adjust its own growth patterns to facilitate optimum translocation of nutrients to new shoots in their different stages of growing in the plant) and formulating interrelations at these functional units and their scalable compositions as well as their applications in different contexts.

In accordance with the present innovation, these novel techniques that adopt these interruptions to the obtaining information as well as processes in the subject process environment as mentioned supra, that are effected at microscopic scale (e.g. elemental unit, conductive units) facilitate establishing interrelations and their patterns with selected processes that occur in microscopic scales (e.g. quantified extents of electrostatic repulsion between two complementary DNA strands in an animal organ cell) upon a common temporal basis that adopts the variable operational step of the computing component (250) and the statistical and probabilistic analytical engines (275). These dynamically established interrelations and their patterns among the respective temporal states of different processes, including those in microscopic scales in a process environment enables utilizing the differentiations of said temporal states and their patterns for a wide range of applications and purposes.

Applications of some of the abovementioned key aspects of the present innovation can be further illustrated while emphasizing that by no means they are exhaustive or defining or confining the scope of its applicability.

As mentioned above, in one key aspect of the present innovation, in obtaining information on a plurality of processes for coordinating processes in the process environment (001) commencing said obtaining of the respective information occur upon receiving signals from the relevant signaling components (225) in the process information devices (150) by the process coordinating component (101). While initiating obtaining information on selected processes the computing component (250) and the statistical and probabilistic analytical engines (275) analyse the selected pluralities of reference characteristics of each of the plurality of information upon their receiving at the respective characteristic identifying components (224) in the processing components (221) of the process information devices (150) in order to establish the interrelations and the patterns of these interrelations of said characteristics of the information in terms of the variable operational step of said computing component (250).

In obtaining information for coordinating processes in a process environment (e.g. skeletal muscle cells in a thigh), in one key aspect of the present innovation, a plurality of characteristic identifying components (224) identify the respective characteristics of a plurality of information on selected processes including flow of epinephrine to the muscle cells due to an environmental stress, increased intracellular breakdown of glycogen to glucose in selected functional units (300), namely, selected skeletal muscle cells in a thigh, protein kinase A initiating a signal transduction cascade, cyclic AMP binding and activating protein kinase A.

The novel techniques, in accordance with the present innovation, thus obtain information at the respective process information devices (150), identified by the corresponding reference characteristic identifying components (224) and received by the respective reference characteristic receiving components (226), based on the instructions of the computing component (250) and the statistical and probabilistic analytical engines (275). In accordance with the present innovation in a process environment such as a thigh muscle of a person, information on protein kinase A initiating a series of intracellular signal transduction cascade due to flow of epinephrine to the functional units (300) (e.g. segments of skeletal muscle tissue or similar segments), as well as on properties of increased cellular energy level in the selected functional units (e.g. muscle tissues) of the thigh due to breakdown of glycogen to glucose, as well as the associated increase in flow of oxygen with blood cells at the respective locations, among other selected associating processes are obtained, mentioned supra. The resulting muscle energy at selected functional units (300)—segments of muscle tissues—in the process environment and the facets of kinetic energy (e.g. movement of thigh as a whole initiated by the muscle tissues and the muscle) are also gathered in terms of the variable operational step of the computing component and the statistical and probabilistic analytical engines, in order to facilitate analysis and identifying interrelations and their patterns among selected processes. As elaborated in this application, these novel techniques thus enable analyzing and formulating interrelations of a wide range of processes ranging from biological and physiological processes of organs (or any other part of a genetic compound carrying entity), genetic activities uniquely specific to an individual person, animal or any other genetic compound carrying entity including viruses as well as the specific macro and micro external factors (e.g. external environmental stress stimuli, intake of medicine or food) that are either short, medium or long term temporally that are related to said selected processes. Methods and instruments for obtaining these values of information required for analysis and establishing interrelations and their patterns in vivo as well as in vitro, at inter cellular and intra cellular scales including in molecular scales in order to identify and receive their respective characteristics as required for application of the present innovation by a plurality of components (224) and components (226) in terms of the variable operational step of the computing component (250) are available in the market and can also be found in published scientific literature.

In accordance with the present innovation, as mentioned above, these novel instruments utilising the novel features in obtaining information on processes that occur in temporal extents lesser than the shortest variable of the variable operational step of the computing component (250) and the statistical and probabilistic analytical engines (275) outline a basis for establishing said processes as quantifiable entities in terms of a common temporal and resource framework adopting said variable operational step of the component (250). These novel techniques adopting said framework as well establish the interrelations and their patterns of identified associated processes at functional units of different scales, which in turn, facilitate disclosing differentiations in temporal states and a selection of resource utilisation and outcome during their operations in different practical applications enabling improved process coordination. The robust basis provided by the novel instruments adopted in the subject innovation enables establishing these differentiations theoretically at n extent of functional units from microscopic to macro scales as suited for process coordination in the respective applications, wherein n is any integer equal to or greater than one.

By establishing collectives of temporal states of stimuli of epinephrine at different functional units in a skeletal muscle in a leg of a person such as selected segments of receptors that bind epinephrine in muscle tissues, for example, the differentiations among said collectives of temporal states, resource utilisation and outcome with those of the associated processes such as interaction of activated receptors with a G protein in a tissue cell, activated G protein in turn activating enzyme adenylate cyclase and the intracellular breakdown of glycogen to glucose as well as at a different temporal scale, the increased leg muscle movement bringing kinetic energy to the person can be formulated, utilising the novel instruments in the present innovation that adopt the variable operational step of the computing component (250) of the system (100).

The temporal and resource differentiations among the processes that can be established in terms of the above bases, in accordance with the present innovation, include a plurality of chemical operations, that involve formation and modification of a wide range of intra and inter atomic bonds involving a variety of molecular and sub molecular scale particle behavior and energy forms, as evidenced through the outline of application in a cellular and intracellular process environment, mentioned supra.

Establishing the collectives of temporal states of the selected operations in process environments that involve intra and inter atomic bonds, in relation to those of the associated processes as well as the values of a selection of such properties and the durations of maintaining these values, in accordance with the present innovation, facilitate deriving an array of benefits, in a wide range of contexts, including chemical energy, medical and pharmacological applications as well as in biological, botanical, genetics and in nano technological applications among others bringing significant practical advantages in a wide range of fields and industries.

In accordance with the present innovation, the novel instruments that formulate these differentiations facilitate establishing vital bases for practical application by system (100) in a context specific manner. As the above mentioned differentiations touch upon the temporal dimension, resource utilization across different forms and types as well as outcome, in one key aspect of the present innovation, such applications can be dynamically tailored not only to suit the field (e.g. agriculture, pharmacology) but the specific context (e.g. watermelon fruit growth in an extremely low rainfall year or medicine with minimal side effects for prevention of molecular interaction that initiates mutation of G protein Ras in lungs to suit the genetics of a particular patient) of its application.

Establishing context specific periodic interruptions to selected processes in a process environment for temporal extents dynamically formulated by the system (100) is one such vital application of the novel instruments. In applications such as those associated with genetics and treatment of diseases (e.g. hypertension) these novel instruments facilitate effecting these periodic interruptions based on the abovementioned differentiations in temporal and resource usage scales while maintaining their respective physiological standards as well as addressing wider implications in genetic and other side effects bringing numerous advantages in optimising outcome through process coordination. It is widely acknowledged that the group of medicines commonly termed Calcium channel blockers (CCB), for example, is effective in interrupting—blocking—the inward movement of Calcium ions that facilitate contracting the heart muscle cells, thereby performing a vital role in decreasing cardiac contractility, among other benefits, for a person suffering from hypertension. However, the monitoring of the administering of CCB in specific muscles and tissues (and in arteries) as well as the temporal extents and scales of their interruptions in the specific heart muscle cells, even in life threatening situations, remain limited to overall observations (e.g. systolic and diastolic blood pressure, heart rate) on the patient.

In conducting process coordination, a plurality of characteristics of the information on these processes and their respective associated processes are obtained and transferred by the respective reference characteristic identifying (224) and receiving (226) and modificating (227) components while the components (280) assist in conducting error handling of these transfers as well. These novel instruments adopting the analysis of this information utilising the dynamically varied references for the respective characteristics, mentioned supra, facilitate formulating the interrelations and their patterns among the selected processes such as Calcium channel antagonist molecules binding at the specific binding sites of respective L-type Calcium channels, the cellular contractility rate as well as the respective Calcium ion concentrations among others, formulate the temporal and cellular extent of the blocking—or interruption—of the inward movement of the Calcium ions.

In accordance with the present innovation, utilising the temporal and resource differentiations among selected processes, these novel techniques formulate the specific temporal and cellular extents of the interruptions effected by a specific extent of medication commonly known as Calcium channel blocker drugs to the movement of Calcium ions through the calcium channels in a selected group of functional units (300), namely, a plurality of cells in a heart muscle of a person administered with the medicine. In one key aspect of the present innovation, the novel instruments, based on the interrelations and their patterns of the processes at the relevant functional unit (300) scale (e.g. section of a heart muscle tissue), adopt the computing component (250) and the statistical and probabilistic engines (275) to initiate the instructions to the respective activating components (280) to transfer the information to the controlling component (290) for the commencement and the interruption of the administering of the medicine to be transported to the functional units (300) while adopting the relevant procedures on medical safety and operational standards that govern the system (100).

Similar applications of these novel instruments to formulate other cellular and intracellular behavior in different kingdoms of cells as well as genetics related processes in viruses in terms of their respective temporal and resource differentiations in order to effect periodic interruptions in selected temporal extents for the relevant processes in a scalable manner (e.g. at cellular scale in muscle tissue to the supply of nutrient supplements in drinking water to livestock in a large farm to release of different molecules of pollen in air) for bringing specific and quantifiable benefits and advantages in a wide range of fields from environmental monitoring to genetics based disease prevention.

What is described above includes only a few examples of the application of the subject matter of the present innovation. It is evidently not practicable to enumerate every possible combination of compositions or, methodologies for the purpose of providing a description of the present innovation, but a person skilled in the art would recognize that many further combinations and permutations of the innovation are possible. The present innovation is intended to embrace all such alterations, modifications and variations that come within the spirit and scope of the appended claims, accordingly. Furthermore, to the extent that the term 'includes' is used, either in the detailed descriptions or in the claims, such term is intended to be inclusive in a manner similar to the term 'comprising' as 'comprising' is interpreted, when employed as a transitional word in a claim.

What is claimed is:

1. A system that facilitates process management in a process environment comprising:
    a processor;
    a plurality of process information devices, run on the processor, adapted to transfer data on operation of a plurality of predetermined processes in a process environment that occur in durations lesser than the shortest temporal extent of the variable operational step of a process coordinating component; the process coordinating component which further comprises a computing component adapted to employ at least one of a plurality of statistical and probabilistic analytical engines that, generate inferences for action, wherein the computing component and the statistical and probabilistic analytical engines include a variable operational step of which the shortest variable operates in a duration lesser than the smallest temporal extent of the transition from one predetermined electromagnetic property level to another predetermined electromagnetic property level upon effecting the variations in supply of external electrical energy to each of a plurality of elemental units; and
    the process coordinating component adapted to effect a plurality of periodic interruptions to obtaining of information on operation of at least one of the processes that occur in durations lesser than the shortest variable of the variable operational step of the computing component.

2. The system of claim 1, the computing component is connected to a plurality of process information devices each of which includes a reference information identifying component and a reference information receiving component adapted to be embedded in vivo in a functional unit.

3. A computer-implemented method for facilitating process coordinating in a process environment, comprising:
    analyzing a plurality of information on a plurality of predetermined processes in a process environment based at least in part upon a framework that establishes each of a plurality of interruptions in selected temporal extents to transfer of information on operation of a plurality of predetermined processes in the process environment that occur in durations lesser than the shortest temporal extent of the variable operational step of a computing component and statistical and probabilistic analytical engines that operates in a duration lesser than the smallest temporal extent of the transition from one predetermined electromagnetic property level to another predetermined electromagnetic property level upon effecting the variations in supply of external electrical energy to each of a plurality of elemental units; and providing a basis for formulating a plurality of interrelations and a plurality of patterns of the interrelations of the predetermined processes based at least in part upon the framework adopted for the analysis of the information.

4. The computer-implemented method of claim 3, further comprising formulating the interrelations and the patterns of the interrelations of operation of each of the processes; and the interrelations and the patterns of the interrelations of each of a plurality of predetermined associating processes based at least in part upon the framework for establishing the interruptions.

5. The computer-implemented method of claim 3, further comprising analyzing a plurality of reference characteristics; and formulating the interrelations and patterns of interrelations of each of the references adopted for analyzing each of the plurality of reference characteristics of the information.

6. The computer-implemented method of 3, further comprising effecting each of the interruptions to and commencement of receiving each of the selected characteristics of the information on the operation of the predetermined processes.

7. The computer-implemented method of claim 3, further comprising effecting a plurality of variations in the selected characteristics of the information on the operation of the predetermined processes.

8. The computer-implemented method of claim 3, further effecting each of the interruptions and each of the commencements of operation of selected processes at a plurality of functional units.

9. The computer-implemented method of claim 3, further comprising providing a basis for establishing interrelations and their patterns of a selection of predetermined levels of selected properties at each of the temporal extents upon effecting the interruptions and resuming of operation of each of the processes for each of a plurality of compositions of each of the plurality of functional units.

10. A computer executable system that facilitates process coordination in a process environment, comprising:

computer-implemented means for establishing a basis for coordination of operation of a plurality of predetermined processes that occur in durations lesser than the shortest temporal extent of the variable operational step of the computing component and the statistical and probabilistic analytical engines that operates in a duration lesser than the smallest temporal extent of the transition from one predetermined electromagnetic property level to another predetermined electromagnetic property level upon effecting the variations in supply of external electrical energy to each of a plurality of elemental units based at least in part upon a framework that determines each of a plurality of interruptions to obtaining information on operation of selected processes; computer-implemented means for, generating a plurality of instructions for operating the selected processes in the process environment based at least in part upon the basis for coordination; and providing a basis for formulating a plurality of interrelations and a plurality of patterns of the interrelations of the predetermined processes based at least in part upon the framework adopted for analysis of the information.

11. The computer-executable system of claim 10, further comprising means for establishing the basis for coordination of operation of a plurality of predetermined processes in relation to at least one of the selected functional units in the process environment based at least in part upon the framework that formulates the interruptions.

12. The computer-executable system of claim 11, further comprising means for functionally interconnecting a plurality of selected functional units in the process environment at each of a plurality of temporal extents, whereby each of the functionally interconnected units facilitates operation of a plurality of selected processes at predetermined operational standards utilizing predetermined resources for predetermined durations.

13. The computer-executable system of claim 10, further comprising means for implementing a plurality of safety and operational procedures in conducting process coordination.

* * * * *

UNITED STATES PATENT AND TRADEMARK OFFICE
CERTIFICATE OF CORRECTION

PATENT NO. : 9,501,317 B2  
APPLICATION NO. : 14/433509  
DATED : November 22, 2016  
INVENTOR(S) : Kuruppu et al.

Page 1 of 1

It is certified that error appears in the above-identified patent and that said Letters Patent is hereby corrected as shown below:

On the Title Page

Item (71) Applicants, should read:  
--(71) Applicant: Indrajith Kuruppu, Wrestedt (DE)--

Signed and Sealed this  
Second Day of May, 2017

Michelle K. Lee  
*Director of the United States Patent and Trademark Office*